United States Patent [19]

Jones et al.

[11] 4,443,647

[45] Apr. 17, 1984

[54] METHANE CONVERSION

[75] Inventors: C. Andrew Jones, Newtown Square; John J. Leonard, Springfield; John A. Sofranko, West Chester, all of Pa.

[73] Assignee: Atlantic Richfield Company, Los Angeles, Calif.

[21] Appl. No.: 522,877

[22] Filed: Aug. 12, 1983

Related U.S. Application Data

[63] Continuation-in-part of Ser. No. 412,664, Aug. 30, 1982.

[51] Int. Cl.$^3$ ................................................ C07C 2/00
[52] U.S. Cl. .................................... 585/500; 585/400; 585/417; 585/541; 585/654; 585/658; 585/700; 585/943
[58] Field of Search ............... 585/500, 700, 541, 654, 585/658, 943, 400, 417

[56] References Cited

U.S. PATENT DOCUMENTS

| | | | |
|---|---|---|---|
| 1,995,136 | 3/1935 | Winkler et al. | 585/500 |
| 2,216,130 | 10/1940 | Pier et al. | 585/943 |
| 2,326,799 | 8/1943 | Pier et al. | 585/700 |
| 2,608,534 | 8/1952 | Fleck | 585/654 |
| 3,900,525 | 8/1975 | Christman et al. | 585/541 |
| 4,066,704 | 1/1978 | Harris et al. | 585/658 |
| 4,205,194 | 5/1980 | Mitchell et al. | 585/500 |
| 4,239,658 | 12/1980 | Mitchell et al. | 585/500 |

*Primary Examiner*—Delbert E. Gantz
*Assistant Examiner*—Cynthia A. Prezlock
*Attorney, Agent, or Firm*—Craig E. Larson

[57] ABSTRACT

A method for synthesizing hydrocarbons from a methane source which comprises contacting methane with an oxide of lead at a temperature of about 500° to 1000° C. The oxide is reduced by the contact and coproduct water is formed. A reducible oxide of lead is regenerated by oxidizing the reduced composition with molecular oxygen. The oxide PbO is a particularly effective synthesizing agent.

22 Claims, 3 Drawing Figures

METHANE CONVERSION

CROSS REFERENCED TO RELATED CASES

This application is a continuation-in-part of U.S. Application Ser. No. 412,664, filed Aug. 30, 1982.

This application is related to copending, concurrently-filed U.S. Patent Application Ser. Nos. 522,994; 522,942; 522,905; 522,877; 522,876; 522,906; 522,935; and 522,938, the entire contents of which are incorporated herein by reference.

BACKGROUND OF THE INVENTION

1. Field of the Invention

This invention relates to synthesis of hydrocarbons from a methane source. A particular application of this invention is a method for converting natural gas to more readily transportable material.

2. Description of the Prior Art

A major source of methane is natural gas. Other sources of methane have been considered for fuel supply, e.g., the methane present in coal deposits or formed during mining operations. Relatively small amounts of methane are also produced in various petroleum processes.

The composition of natural gas at the wellhead varies but the major hydrocarbon present is methane. For example the methane content of natural gas may vary within the range of from about 40 to 95 vol. %. Other constituents of natural gas may include ethane, propane, butanes, pentane (and heavier hydrocarbons), hydrogen sulfide, carbon dioxide, helium and nitrogen.

Natural gas is classified as dry or wet depending upon the amount of condensable hydrocarbons contained in it. Condensable hydrocarbons generally comprise $C_{3}+$ hydrocarbons although some ethane may be included. Gas conditioning is required to alter the composition of wellhead gas, processing facilities usually being located in or near the production fields. Conventional processing of wellhead natural gas yields processed natural gas containing at least a major amount of methane.

Large-scale use of natural gas often requires a sophisticated and extensive pipeline system. Liquefaction has also been employed as a transportation means, but processes for liquefying, transporting, and revaporizing natural gas are complex, energy-intensive, and require extensive safety precautions. Transport of natural gas has been a continuing problem in the exploitation of natural gas resources. It would be extremely valuable to be able to convert methane (e.g., natural gas) to more easily handleable, or transportable, products. Moreover, direct conversion to olefins such as ethylene or propylene would be extremely valuable to the chemical industry.

In addition to its use as fuel, methane is used for the production of halogenated products (e.g., methyl chloride, methylene chloride, chloroform and carbon tetrachloride). Methane has also been used as a feedstock for producing acetylene by electric-arc or partial-oxidation processes. Electric-arc processes are operated commercially in Europe. In partial-oxidation processes, a feed mixture of oxygen and methane (the methane may contain other, additional hydrocarbons) are preheated to about 540° C. and ignited in a burner. Representative processes of this type are disclosed in U.S. Pat. Nos. 2,679,544; 3,234,300; and 3,244,765. Partial oxidation produces significant quantities of CO, $CO_2$ and $H_2$, yielding a dilute acetylene-containing gas and thereby making acetylene recovery difficult.

The largest, non-fuel use of methane is in the production of ammonia and methanol (and formaldehyde). The first, methane conversion, step of these processes is the production of a synthesis gas ($CO+H_2$) by reforming of methane in the presence of steam over, for example, a nickel catalyst. Typical reformers are tubular furnaces heated with natural gas, the temperature being maintained at 900° C. and the pressure at about 225 atmospheres.

Pyrolytic or dehydrogenative conversion of methane or natural gas to $C_{2}+$ hydrocarbons has previously been proposed. The conversion requires high temperatures (greater than about 1000° C.) and is characterized by the formation of by-product hydrogen. The patent literature contains a number of proposals to catalyze pyrolytic reactions, allowing conversion at lower temperatures. See, for example, U.S. Pat. Nos. 1,656,813; 1,687,890; 1,851,726; 1,863,212; 1,922,918; 1,945,960; 1,958,648; 1,986,238 and 1,988,873. U.S. Pat. No. 2,436,595 discloses and claims a catalytic, dehydrogenative methane-conversion process which employs fluidized beds of heterogeneous catalysts comprising an oxide or other compound of the metals of group VI or VIII.

Including oxygen in a methane feed for conversion over metal oxide catalysts has been proposed. Margolis, L. Ya., Adv. Catal. 14, 429 (1963) and Andtushkevich, T. V., et al, Kinet. Katal. 6, 860 (1965) studied oxygen/methane cofeed over different metal oxides. They report the formation of methanol, formaldehyde, carbon monoxide and carbon dioxide from methane/oxygen feeds. Higher hydrocarbons are either not formed or are converted much faster than methane.

SUMMARY OF THE INVENTION

It has been found that methane may be converted to higher hydrocarbon products by contacting a methane-containing gas with an oxide of lead at temperatures within the range of about 500° to 1000° C. Hydrocarbons produced include lower alkanes, lower olefins, and aromatics. The oxide of lead is reduced by the methane contact and is easily reoxidizable by contact with an oxygen-containing gas. PbO is a preferred oxide of lead.

The present process is distinguished from previously known pyrolytic methane conversion processes by the use of reducible lead oxide to synthesize higher hydrocarbons from methane with coproduction of water, rather than hydrogen.

The present process is also distinguished from previously suggested methane conversion processes which rely primarily on interactions between methane and at least one of nickel and the noble metals, such as rhodium, palladium, silver, osmium, iridium, platinum and gold. An example of this type of process is disclosed in U.S. Pat. No. 4,205,194. The present process does not require that methane be contacted with one or more of nickel and such nobel metals and compounds thereof.

Moreover, in a preferred embodiment, such contacting is carried out in the substantial absence of catalytically effective nickel and the noble metals and compounds thereof to minimize the deleterious catalytic effects of such metals and compounds thereof. For example, at the conditions, e.g., temperatures, useful for the contacting step of the present invention, these metals when contacted with methane tend to promote coke formation, and the metal oxides when contacted with methane tend to promote formation of combustion products (CO$_x$) rather than the desired hydrocarbons. The term "catalytically effective" is used herein to identify that quantity of one or more of nickel and the noble metals and compounds thereof which when present substantially changes the distribution of products obtained in the contacting step of this invention relative to such contacting in the absence of such metals and compounds thereof.

This invention is further described in the following description of its presently preferred embodiments.

DETAILED DESCRIPTION OF THE INVENTION

Figure 1:
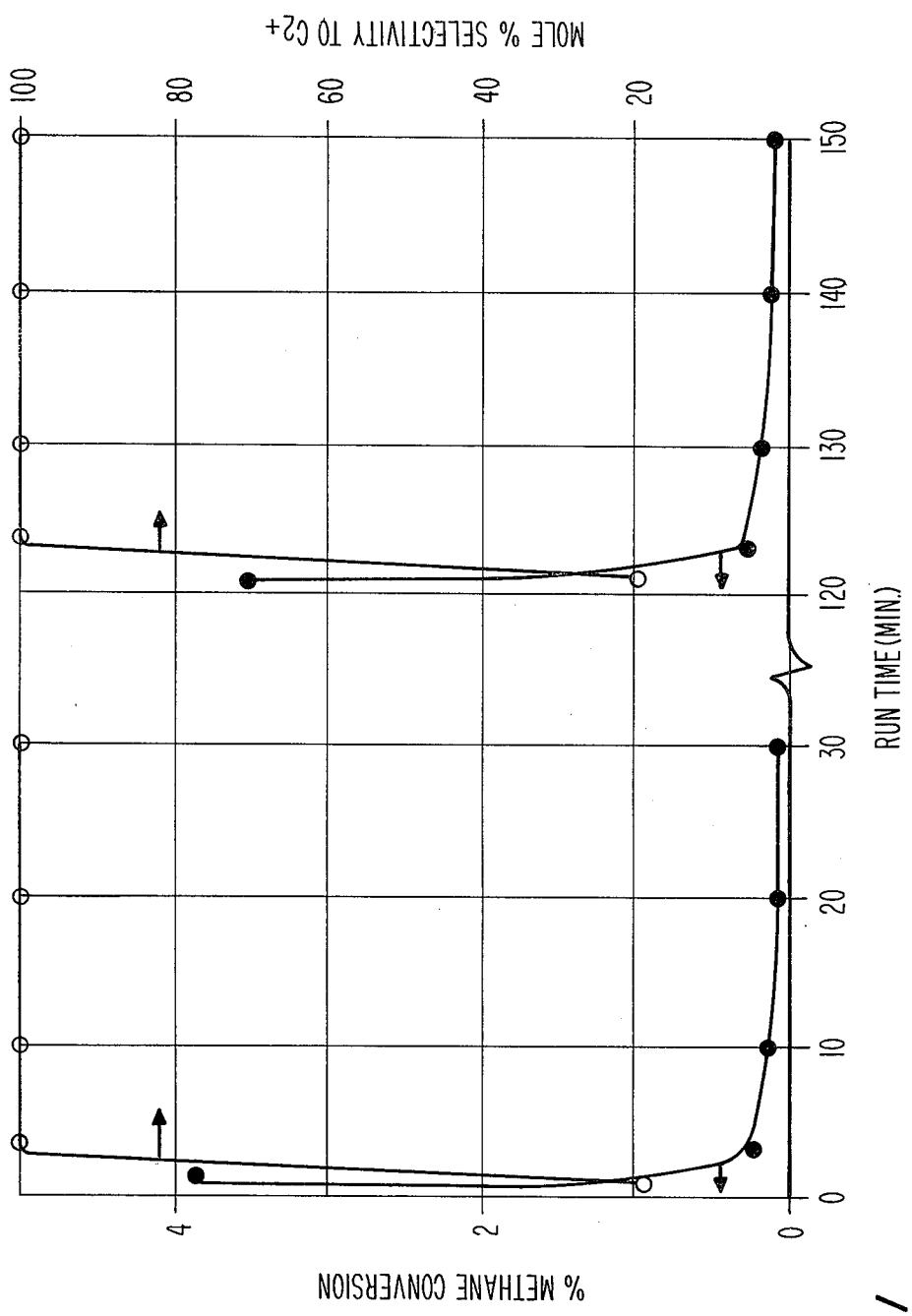
FIG. 1 is a plot of methane conversion and hydrocarbon selectivity vs. time for the results of Examples 1 and 2.

Reducible oxides of lead can be supplied from a variety of known sources. The term "reducible" is used to identify those oxides of lead which are reduced by contact with methane at temperatures in the range of about 500° to 1000° C. Among the reducible oxides of lead, those containing major amounts of PbO are preferred.

The reducible oxide of lead is preferably provided as solid particles. It may be supported by, or diluted with, a conventional support material such as silica, alumina, titania, zironia, and the like, and combinations thereof. A presently preferred support material is silica.

The term "oxide of lead" includes: (1) one or more lead oxides and/or (2) one or more oxygen-containing compounds of lead, provided that such oxides and compounds have the capability of performing to produce higher hydrocarbon products as set forth herein. The reducible oxides of lead may be employed alone or in combination with reducible oxides of other metals (see copending U.S. Applications Ser. Nos. 522,925; 522,944; 522,942; 522,905; 522,876; and 522,906 and/or oxidative synthesizing agents. Oxidative synthesizing agents are compositions comprising at least one oxide of at least one metal, which composition, when contacted with methane at a temperature selected within the range of about 500° to 1000° C., produces C$_2$+ hydrocarbon products, coproduct water, and a composition comprising a reduced metal oxide.

Solids may be formed in conventional manner using techniques well known to persons skilled in the art. For example, supported solids may be prepared by conventional methods such as adsorption, impregnation, precipitation, coprecipitation, or dry-mixing.

A suitable method is to impregnate the support with solutions of a lead compound. Some examples of lead compounds are the acetate, acetylacetonate, oxide, carbide, carbonate, hydroxide, formate, oxalate, nitrate, phosphate, sulfate, sulfide, tartrate, fluoride, chloride, bromide or iodide. Such compounds of lead may be dissolved in water or other solvent and the solutions are combined with the support and then evaporated to dryness. Preferably, aqueous solutions are employed and water-soluble forms of lead are used. In some cases, the solutions may have acids and/or bases added to them to facilitate dissolution of the precursors of the oxide of lead. For example, acids such as hydrochloric or nitric acid or bases such as ammonium hydroxide may be used as desired. The dried solids may then be screened or otherwise processed to form the desired shape, size, or other physical form of the finished solids. Finally, the solids are prepared for use by calcination at high temperatures for a period of time in accordance with conventional practice in this art. For example, the solids are placed in an oven or kiln, or in a tube through which oxygen (e.g., air or oxygen diluted with other gases) is passed, at an elevated temperature (e.g., about 300° to 1000° C., preferably about 500° to 900° C.). Use of higher calcination temperature promotes the formation of PbO in the finished solid.

The foregoing description regarding preparation of solids in a form suitable for the synthesis of hydrocarbons from a methane source is merely illustrative of many possible preparative methods, although it is a particularly suitable method and is preferred.

Lead loadings on supported solids may be within the range of about 1 to 50 wt. % Pb (calculated as elemental metal).

In addition to methane, the feedstock employed in the method of this invention may contain other hydrocarbon or nonhydrocarbon components, although the methane content should be within the range of about 40 to 100 vol. %, preferably from about 80 to 100 vol. %, more preferably from about 90 to 100 vol. %.

Operating temperatures for the contacting of methane-containing gas and a reducible oxide of lead are in the range of about 500° to 1000° C., preferably within the range of about 600° to 900° C.

Operating pressures for the methane contacting step are not critical to the presently claimed invention. However, both general system pressure and the partial pressure of methane have been found to effect overall results. Copending, concurrently filed U.S. Application Ser. No. 522,935 discloses a method wherein an oxidative synthesizing agent comprising a reducible metal oxide is contacted with methane, the claimed improvement residing in the use of elevated pressures to promote the formation of C$_3$+ hydrocarbon products.

Contacting methane and a reducible oxide of lead to synthesize higher hydrocarbons also produces a reduced oxide of lead and coproduct water. The exact nature of the reduced form of the synthesizing agent is unknown, and so is referred to herein as "reduced oxide of lead". Regeneration of the reducible oxide of lead is readily accomplished by contacting reduced solids with oxygen (e.g., an oxygen-containing gas such as air). Oxygen contacting temperatures are preferably within the range of about 300° to 1000° C., more preferably within the range of about 500° to 900° C. Higher reoxidation temperatures promote the formation of PbO, the preferred reducible oxide of lead.

A single reactor apparatus containing a fixed bed of solids, for example, may be used with intermittent or pulsed flow of a first gas comprising methane and a second gas comprising oxygen (e.g., oxygen, oxygen diluted with an inert gas, or air, preferably air).

Preferably, the methane contacting step and the oxygen contacting step are performed in physically separate zones with solids recirculating between the two zones. Thus, a suitable method for synthesizing hydrocarbons from a methane source comprises: (a) contacting a gas comprising methane and particles comprising a reducible oxide of lead to form higher hydrocarbon products, coproduct water, and particles comprising a reduced oxide of lead; (b) removing particles comprising a reduced oxide of lead from step (a) and contacting the reduced solids with an oxygen-containing gas to form particles comprising a reducible oxide of lead; and (c) returning particles comprising a reducible oxide of lead formed in step (b) to step (a). Steps (a), (b) and (c) are preferably repeated at least periodically, and more preferably the steps are continuous. Thus, in this more preferred embodiment, solids are continuously circulated between at least one methane-contact zone and at least one oxygen contact zone. This more preferred embodimetn is disclosed and claimed in copending, concurrently filed U.S. Application Ser. No. 522,938.

Particles comprising a reducible oxide of lead may be contacted with methane in fixed, moving, fluidized, ebullating, or entrained beds of solids. Preferably, methane is contacted with a fluidized bed of particles.

Similarly, particles comprising a reduced oxide of lead may be contacted with oxygen in fixed, moving, fluidized, ebullating or entrained beds of solids. Preferably, oxygen is contacted with a fluidized bed of particles.

The invention is further illustrated by reference to the following examples.

Experimental results (conversions and selectivities) are reported on a molar basis.

EXAMPLE 1

Lead (II) acetate (0.92 gram) was dissolved in 100 ml. of water. This solution was added to 9.5 grams of Houdry HSC 534 silica and allowed to stand for one hour. The mixture was slowly taken to dryness with gentle warming, followed by heating at 110° C. in a drying oven for 2 hours. The solid was then heated to 500° C. at a rate of 2° C./minute and held at 500° C. for 10 hours to give a finished solid containing 5 wt. % lead.

The finished solid (2.8 grams) was charged to a quartz tube (0.5 inch inside diameter) surrounded by a tubular furnace. The reactor temperature was raised to 700° C. under flowing nitrogen. Nitrogen flow was stopped and methane was introduced into the reactor at a rate of 100 ml./min. (860 hrs.$^{-1}$ GHSV). The reactor effluent was sampled at the reactor exit and analyzed on a gas chromatograph at a number of time intervals. In addition, all reactor effluent was collected in a sample bag for subsequent analysis of the cumulative reaction products. Results (obtained at about atmospheric pressure and 700° C.) are shown in Table I below. The total amount of carbon oxides formed during reoxidation of the solids (see Example 2, infra) was used to calculate the yield of coke (or other carbonaceous deposit) formed on the solid during the methane run. The instantaneous results shown in Table I are methane conversion to gaseous products and selectivity to these products (i.e., % of C converted to gas phase products). The cumulative results shown in Table I include solid formation.

TABLE 1

| Run Time (min.) | % Conversion | Selectivity* | | | | | | | |
|---|---|---|---|---|---|---|---|---|---|
| | | $C_2H_4$ | $C_2H_6$ | $C_3$ | $C_{4,5}$ | Benzene | CO | $CO_2$ | Coke* |
| Instantaneous Results | | | | | | | | | |
| 1 | 3.87 | 12.4 | 5.7 | 0.5 | 0.3 | 0.2 | 61.7 | 19.1 | |
| 3 | 0.26 | 62.5 | 33.6 | 2.7 | 1.2 | 0.0 | 0.0 | 0.0 | |
| 10 | 0.12 | 61.9 | 38.1 | 0.0 | 0.0 | 0.0 | 0.0 | 0.0 | |
| 20 | 0.08 | 58.3 | 41.7 | 0.0 | 0.0 | 0.0 | 0.0 | 0.0 | |
| 30 | 0.08 | 57.5 | 42.5 | 0.0 | 0.0 | 0.0 | 0.0 | 0.0 | |
| Cumulative Results | | | | | | | | | |
| 30 | 0.33 | 23.1 | 14.9 | 0.3 | 0.2 | 0.1 | 24.0 | 7.5 | 29.9 |

*Basis of instantaneous results is C converted to gas phase products and does not include conversion to solid, carbonaceous deposits.

EXAMPLE 2

After completion of the run described in Example 1, the reactor was flushed with nitrogen for 30 minutes and the solid was reoxidized under flowing air at 700° C. for 90 minutes. The reoxidized solid was then contacted with methane in the same manner described in Example 1. Results, shown in Table II below, are presented as in Example 1. FIG. 1 is a plot of methane conversion to gaseous products and $C_2+$ hydrocarbon product selectivity (basis: methane conversion to gaseous products) vs. run time for the combined results of Examples 1 and 2.

TABLE II

| Run Time (min.) | % Conversion | % Selectivity* | | | | | | | |
|---|---|---|---|---|---|---|---|---|---|
| | | $C_2H_4$ | $C_2H_6$ | $C_3$ | $C_{4,5}$ | Benzene | CO | $CO_2$ | Coke* |
| Instantaneous Results | | | | | | | | | |
| 1 | 3.50 | 14.3 | 5.2 | 0.2 | 0.1 | 0.1 | 62.9 | 17.2 | |
| 3 | 0.29 | 54.1 | 43.9 | 1.0 | 0.7 | 0.3 | 0.0 | 0.0 | |
| 10 | 0.16 | 51.2 | 48.0 | 0.8 | 0.0 | 0.0 | 0.0 | 0.0 | |
| 20 | 0.11 | 51.4 | 48.6 | 0.0 | 0.0 | 0.0 | 0.0 | 0.0 | |
| 30 | 0.10 | 51.0 | 49.0 | 0.0 | 0.0 | 0.0 | 0.0 | 0.0 | |
| Cumulative Results | | | | | | | | | |
| 30 | 0.31 | 25.3 | 23.1 | 0.5 | 0.3 | 0.1 | 19.2 | 7.4 | 25.0 |

*Basis of instantaneous results is C converted to gas phase products and does not include conversion to solid, carbonaceous deposits.

EXAMPLE 3

Figure 2:
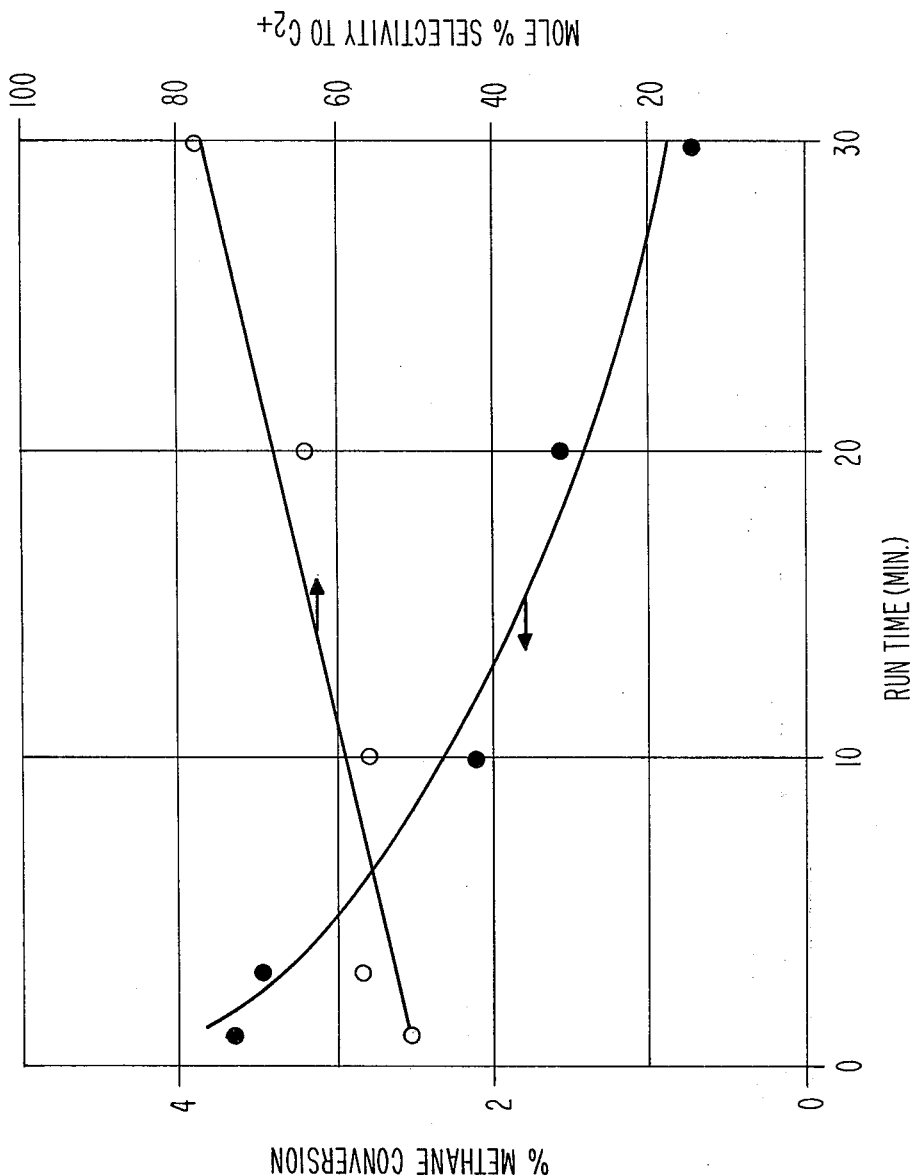
FIG. 2 is a plot of methane conversion and hydrocarbon product selectivity vs. time for the results of Example 3.

Example 1 was repeated except that the GHSV was 86 hrs.$^{-1}$. Results are shown in Table III below and are plotted as a function of run time in FIG. 2.

TABLE III

| Run Time (min.) | % Conversion | % Selectivity* | | | | | | | | |
|---|---|---|---|---|---|---|---|---|---|---|
| | | $C_2H_4$ | $C_2H_6$ | $C_3$ | $C_{4,5}$ | Benzene | Toluene | CO | $CO_2$ | Coke* |
| Instantaneous Results | | | | | | | | | | |
| 1 | 3.66 | 38.6 | 3.6 | 3.3 | 2.4 | 2.9 | 0.8 | 0.0 | 48.4 | |
| 3 | 3.47 | 43.6 | 4.0 | 3.8 | 2.3 | 2.7 | 0.9 | 0.0 | 42.7 | |
| 10 | 2.07 | 43.5 | 4.4 | 3.9 | 2.1 | 1.7 | 0.5 | 0.0 | 43.9 | |
| 20 | 1.57 | 50.3 | 5.4 | 4.5 | 1.8 | 1.3 | 0.4 | 0.0 | 36.3 | |
| 30 | 0.70 | 58.7 | 9.0 | 5.9 | 1.9 | 1.4 | 0.3 | 0.0 | 22.9 | |
| Cumulative Results | | | | | | | | | | |
| 30 | 3.15 | 25.7 | 3.5 | 3.2 | 1.6 | 1.3 | 0.3 | 0.0 | 25.7 | 38.7 |

*Basis of instantaneous results is C converted to gas phase products and does not include conversion to solid, carbonaceous deposits.

EXAMPLE 4

Figure 3:
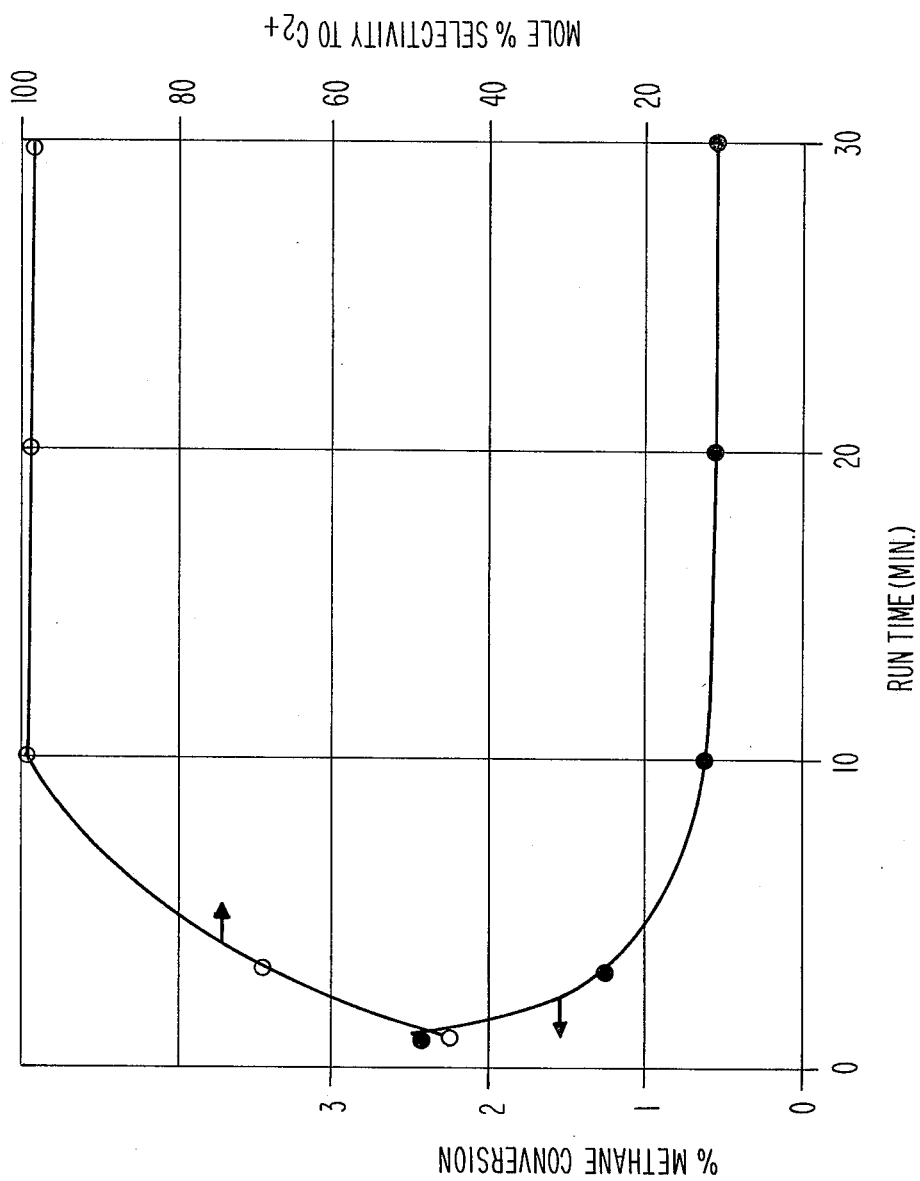
FIG. 3 is a plot of methane conversion and hydrocarbon product selectivity vs. time for the results reported in Example 4.

Example 1 was repeated except that the contact zone temperature was 800° C. Results are shown in Table IV below and are plotted as a function of run time in FIG. 3.

TABLE IV

| Run Time (min) | % Conversion | % Selectivity | | | | | | | | |
|---|---|---|---|---|---|---|---|---|---|---|
| | | $C_2H_4$ | $C_2H_6$ | $C_3$ | $C_{4,5}$ | Benzene | Toluene | CO | $CO_2$ | Coke* |
| Instantaneous Results | | | | | | | | | | |
| 1 | 2.45 | 32.6 | 4.9 | 3.5 | 2.2 | 1.9 | 0.7 | 26.9 | 27.3 | |
| 3 | 1.22 | 49.3 | 9.0 | 4.9 | 2.5 | 2.1 | 0.9 | 31.3. | 0.0 | |
| 10 | 0.63 | 66.3 | 20.3 | 7.2 | 3.0 | 2.5 | 0.7 | 0.0 | 0.0 | |
| 20 | 0.54 | 59.7 | 24.3 | 8.2 | 4.3 | 2.6 | 0.9 | 0.0 | 0.0 | |
| 30 | 0.54 | 58.5 | 25.6 | 9.0 | 3.1 | 2.9 | 0.9 | 0.0 | 0.0 | |
| Cumulative Results | | | | | | | | | | |
| 30 | 1.25 | 38.6 | 12.9 | 4.6 | 2.1 | 1.8 | 0.7 | 4.0 | 1.6 | 33.7 |

*Basis of instantaneous results is C converted to gas phase products and does not include conversion to solid, carbonaceous deposits.

What is claimed is:

1. A method for converting methane to higher hydrocarbon products which comprises contacting a gas comprising methane and a reducible oxide of lead at a temperature within the range of about 500° to 1000° C.

2. The method of claim 1 wherein the reducible oxide is contacted with a gas comprising methane at a temperature within the range of about 600° to 900° C.

3. The method of claim 1 wherein the gas contains about 40 to 100 vol. % methane.

4. The method of claim 3 wherein the gas contains about 80 to 100 vol. % methane.

5. The method of claim 4 wherein the gas contains about 90 to 100 vol. % methane.

6. The method of claim 1 wherein the gas comprising methane is natural gas.

7. The method of claim 1 wherein the gas comprising methane is processed natural gas.

8. The method of claim 1 wherein a gas consisting essentially of methane is contacted with the said reducible oxide.

9. The method of claim 1 wherein the reducible oxide of lead comprises PbO.

10. The method of claim 1 wherein the oxide of lead is associated with a support material.

11. The method of claim 9 wherein the oxide of lead is associated with a support material.

12. The method of claim 10 wherein the support material is silica.

13. The method of claim 11 wherein the support material is silica.

14. A method for synthesizing hydrocarbons from a methane source which comprises:
  (a) contacting a gas comprising methane with a solid comprising a reducible oxide of lead at a temperature within the range of about 500° to 1000° C. to form $C_2+$ hydrocarbons, coproduct water, and solids comprising a reduced oxide of lead; said contacting being carried out in the substantial absence of catalytically effective Ni, Rh, Pd, Ag, Os, Ir, Pt and Au and compounds thereof.
  (b) recovering $C_2+$ hydrocarbons;
  (c) at least periodically contacting the solids comprising a reduced oxide of lead with an oxygen-containing gas to produce a solid comprising a reducible oxide of lead; and
  (d) contacting a gas comprising methane with the solids produced in step (c) as recited in step (a).

15. The method of claim 14 wherein the temperature of step (c) is within the range of about 300° to 1000° C.

16. The method of claim 14 wherein the temperature of step (c) is within the range of about 500° to 900° C.

17. The method of claim 16 wherein the reducible oxide of lead comprises PbO.

18. The method of claim 16 wherein the said solid of step (a) comprises PbO on a silica support.

19. The method of claim 14 wherein solids of step (a) are maintained in the methane-contacting zone as a fluidized bed.

20. The method of claim 19 wherein solids of step (a) are maintained in the oxygen-contacting zone as a fluidized bed.

21. The method of claim 20 wherein the temperature of step (a) is within the range of about 600° to 900° C.

22. The method of claim 21 wherein the temperature of step (c) is within the range of about 500° to 900° C.

* * * * *